United States Patent [19]

Duffett et al.

[11] Patent Number: Plant 5,440

[45] Date of Patent: Apr. 16, 1985

[54] CHRYSANTHEMUM PLANT NAMED BALLERINA

[75] Inventors: William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 514,320

[22] Filed: Jul. 15, 1983

[51] Int. Cl.[3] ..... A01H 5/00

[52] U.S. Cl. ..... Plt./77

[58] Field of Search ..... Plt./77

*Primary Examiner*—Bagwill Robert E.

*Attorney, Agent, or Firm*—Schwartz, Jeffery, Schwaab, Mack, Blumenthal & Koch

[57] ABSTRACT

A chrysanthemum cultivar named Ballerina identified by the combined chacteristics of spider capitulum form, with tubular shaped ray florets, decorative capitulum type, white floret color, diameter across the face of capitulum up to 85 mm., medium plant height, upright branching pattern, average natural season flowering date of September 15, and average flowering response period of seven weeks in photoperiodic controlled short day programs with excellent adaptability and performance in April - May pot mum flowerings.

3 Drawing Figures

The present invention comprises a new and distinct cultivar of *Chrysanthemum morifolium,* Ramat., named Ballerina.

Ballerina is a product of a planned breeding program which had the objective of creating cultivars with decorative capitulum type, spider form, short height, spreading branching pattern, durable inflorescence, 6 to 7 week flowering response period, and white ray floret color under outdoor natural season environments.

Ballerina was originated from a cross made by Grace H. Mack in a controlled breeding program in New Canaan, Conn. in the year 1978. The female parent was an unnamed white flat decorative seedling identified as 76 398-5. The male parent was an unnamed white spider decorative seedling identified as 77 483-4.

Ballerina was discovered and selected as a flowering plant within the progeny of the stated cross by William E. Duffett on Oct. 5, 1979 in an outdoor field in Salinas, Calif. The first act of asexual reproduction of Ballerina was accomplished when vegetative cuttings were taken from the initial selection in February 1980 under procedures formulated and supervised by William E. Duffett. Horticultural examination of selected units initiated June 1980 has demonstrated that the combination of characteristics herein disclosed for Ballerina are firmly fixed and are retained through successive generations of asexual reproduction.

Ballerina has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Ballerina which in combination distinguish this chrysanthemum as a new and distinct cultivar:

(1) Spider capitulum form, with tubular shaped ray florets.

(2) Decorative capitulum type.

(3) White ray floret color.

(4) Diameter across face of capitulum up to 85 mm.

(5) Medium plant height.

(6) Upright branching pattern.

(7) Average natural season flowering date of Sept. 15.

(8) Average flowering response period of seven weeks in photoperiodic controlled short day programs with excellent adaptability and performance in April - May pot mum flowerings.

The accompanying photographic drawings show typical inflorescence and foliage characteristics of Ballerina.

Sheet 1 is a color photograph of Ballerina.

Sheet 2 is a black and white photograph showing three views of the inflorescence of Ballerina.

Sheet 3 is a black and white photograph showing the leaves of Ballerina at three stages of development (mature, intermediate, immature).

Of the many commercially available cultivars known to the present inventors, the most similar existing cultivar in comparison to Ballerina is Patriot, disclosed in U.S. Plant Pat. No. 3,897.

Reference is made to attached Chart A which compares certain characteristics of Ballerina with the same characteristics of Patriot. It will be noted that in comparison to Patriot, Ballerina has spider versus flat capitulum form with tubular versus flat shaped ray florets, larger capitulum diameter and taller plant height. The inflorescence color, upright growth habit and natural season flowering date of Ballerina are similar to those of Patriot.

In the following description, color references are made to The Royal Horticultural Society Colour Chart. The color values were determined between 10:00 A.M. and 10:30 A.M. on Sept. 18, 1982 and May 12, 1983 under 150 foot-candle light intensity at Salinas, Calif.

Botanical classification: *Chrysanthemum morifolium,* Ramat., cv BALLERINA. Early flowering pot and garden mum.

INFLORESCENCE

Capitulum:

*Form.*—Spider having tubular shaped ray florets.

*Type.*—Decorative.

*Permanence.*—Durable up to three weeks. Resists shatter.

*Diameter across face.*—Up to 85 mm.

Corolla of ray florets: White.

*Color (abaxial).*—155B.

*Color (adaxial).*—155D.

Reproductive organs:

*Androecium.*—Present disc florets; pollen scant.

*Gynoecium.*—Present both ray and disc florets.

Corolla of disc florets:

*Color.*—Immature: 2A. Mature: 12A.

PLANT

General appearance: Medium height, strong upright branching habit.

Foliage:

*Color (abaxial).*—147A.

*Color (adaxial).*147B.

Shape: Deep lobed. Moderately serrated.

CHART A

COMPARISON OF BALLERINA AND PATRIOT

| CULTIVAR | RAY FLORET COLOR | CAPITULUM FORM AND TYPE | AVERAGE NATURAL SEASON FLOWER DATE |
|---|---|---|---|
| BALLERNIA | WHITE | SPIDER | SEPTEMBER 15 |
| PATRIOT | IVORY WHITE | DECORATIVE FLAT DECORATIVE | SEPTEMBER 20 |

CHART A-continued

COMPARISON OF BALLERINA AND PATRIOT

| CULTIVAR | PLANT HEIGHT | BRANCHING PATTERN AND SPREAD | DIAMETER ACROSS FACE OF CAPITULUM | PERMANENCE OF FORM & COLOR |
|---|---|---|---|---|
| BALLERNIA | MEDIUM | UPRIGHT | UP TO 85 mm. | UP TO 3 WEEKS |
| PATRIOT | SHORT | UPRIGHT | UP TO 85 mm. | UP TO 3 WEEKS |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., plant named Ballerina, as illustrated and described, and identified by the combined characteristics of spider capitulum form, with tubular shaped ray florets, decorative capitulum type, white ray floret color, diameter across face of capitulum up to 85 mm., medium plant height, upright branching pattern, average natural season flowering date of Sept. 15, and average flowering response period of seven weeks in photoperiodic controlled short day programs.

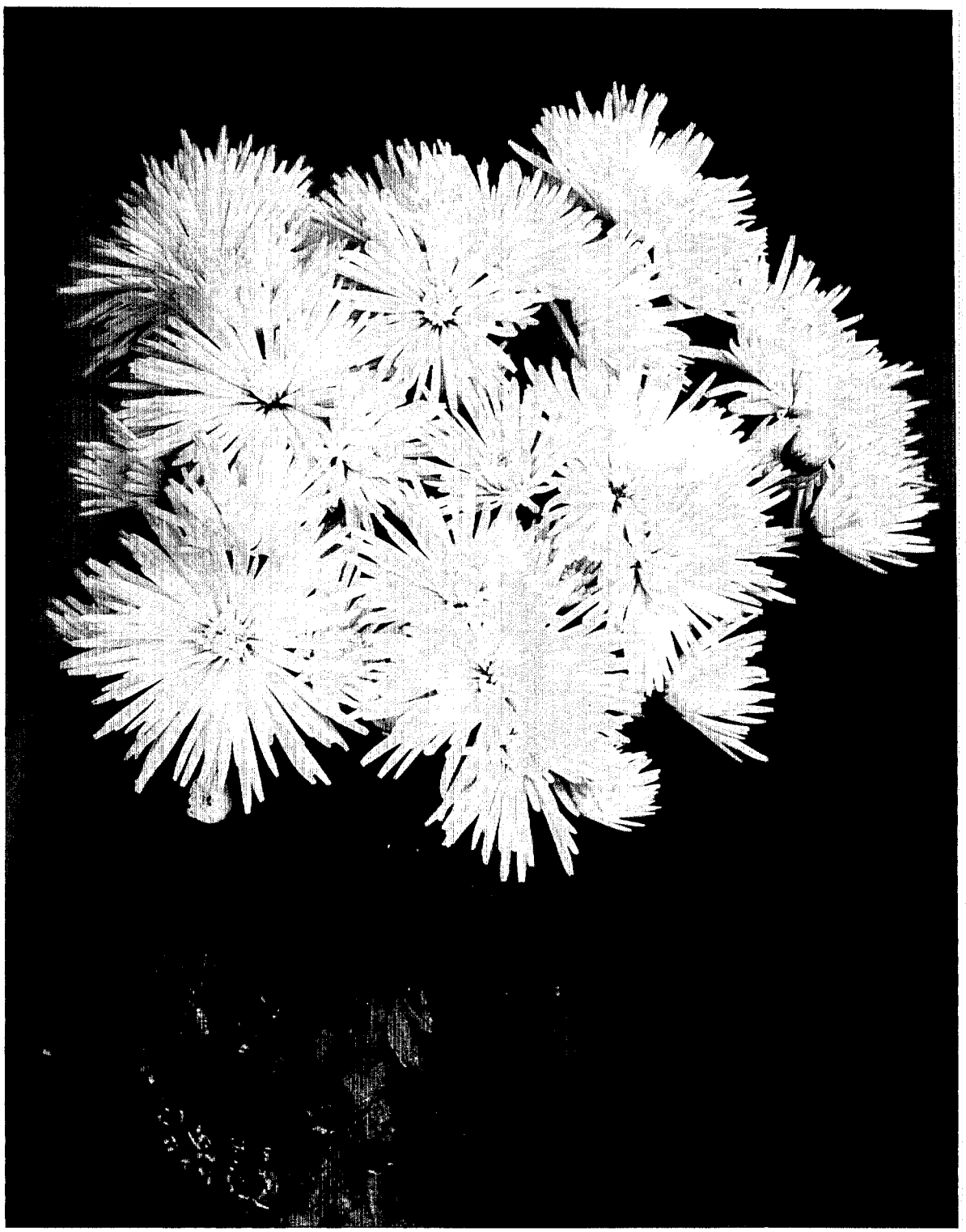

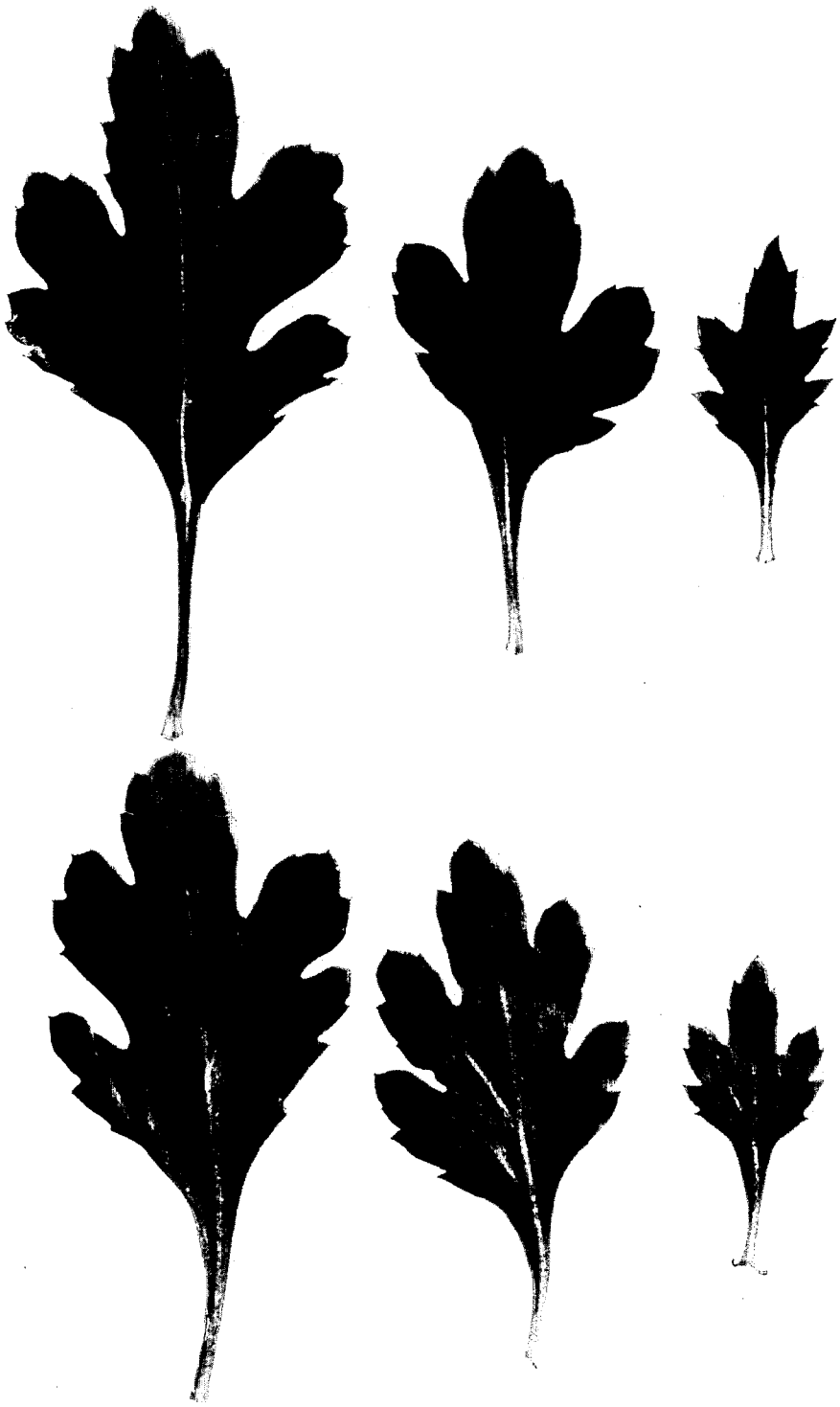

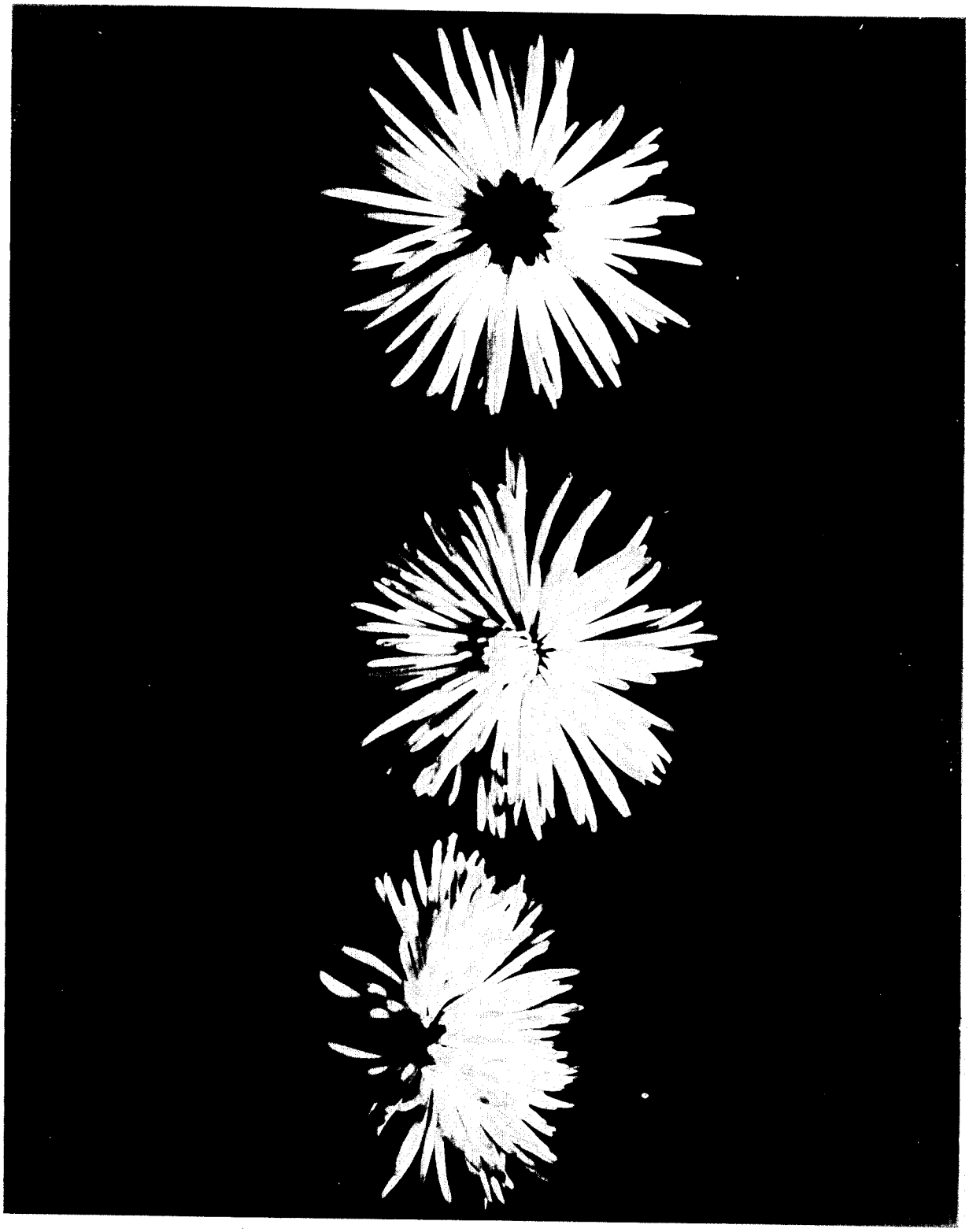

* * * * *